US010293187B2

(12) United States Patent
Cannata et al.

(10) Patent No.: US 10,293,187 B2
(45) Date of Patent: May 21, 2019

(54) HISTOTRIPSY EXCITATION SEQUENCES OPTIMIZED FOR BUBBLE CLOUD FORMATION USING SHOCK SCATTERING

(71) Applicants: Histosonics, Inc., Ann Arbor, MI (US); The Regents of the University of Michigan, Ann Arbor, MI (US)

(72) Inventors: Jonathan M. Cannata, Ann Arbor, MI (US); Timothy L. Hall, Ann Arbor, MI (US); Adam D. Maxwell, Seattle, WA (US); Dejan Teofilovic, Ann Arbor, MI (US)

(73) Assignees: HISTOSONICS, INC., Ann Arbor, MI (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 511 days.

(21) Appl. No.: 14/323,693

(22) Filed: Jul. 3, 2014

(65) Prior Publication Data

US 2015/0011916 A1 Jan. 8, 2015

Related U.S. Application Data

(60) Provisional application No. 61/842,820, filed on Jul. 3, 2013.

(51) Int. Cl.
*A61N 7/00* (2006.01)
*A61B 17/00* (2006.01)
(Continued)

(52) U.S. Cl.
CPC .......... *A61N 7/00* (2013.01); *A61B 17/22004* (2013.01); *A61B 17/225* (2013.01);
(Continued)

(58) Field of Classification Search
CPC .............................. A61N 7/00; A61H 23/0245
See application file for complete search history.

(56) References Cited

U.S. PATENT DOCUMENTS 3,243,497 A 3/1966 Kendall et al.
3,679,021 A 7/1972 Goldberg et al.
(Continued)

FOREIGN PATENT DOCUMENTS

CN 102481164 A 5/2012
DE 3220751 A1 12/1933
(Continued)

OTHER PUBLICATIONS

Maxwell et al., Cavitation clouds created by shock scattering from bubbles during histotripsy, Oct. 2011, J. Acoust. Soc. Am., vol. 130, No. 4, pp. 1888-1898.*

(Continued)

*Primary Examiner* — Hien N Nguyen
(74) *Attorney, Agent, or Firm* — Shay Glenn LLP

(57) ABSTRACT

Methods and devices for producing cavitation in tissue are provided. In one embodiment, a shock scattering method of Histotripsy therapy comprises delivering an initiation pressure waveform from an ultrasound therapy transducer into tissue, the initiation pressure waveform being configured to produce at least one bubble in the tissue, delivering a scattering pressure waveform from the ultrasound therapy transducer into the at least one bubble within a life-cycle of the at least one bubble, and producing cavitation nuclei near the at least one bubble with the scattering pressure waveform. The scattering pressure waveform can be delivered during the life-cycle of the at least one bubble. In some embodiments, the scattering pressure waveform is delivered (Continued)

within 5 µs to 1 s of the initiation pressure waveform. Systems for performing shock scattering Histotripsy therapy are also discussed.

19 Claims, 8 Drawing Sheets

(51) Int. Cl.
  *A61B 17/22* (2006.01)
  *A61B 17/225* (2006.01)
(52) U.S. Cl.
  CPC .............. *A61B 2017/00176* (2013.01); *A61B 2017/22008* (2013.01); *A61B 2017/22028* (2013.01); *A61N 2007/0039* (2013.01); *A61N 2007/0078* (2013.01)

(56) References Cited

U.S. PATENT DOCUMENTS

| | | |
|---|---|---|
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |

(56) References Cited

U.S. PATENT DOCUMENTS

| | | |
|---|---|---|
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 8,057,408 B2 | 11/2011 | Cain et al. |
| 8,333,115 B1 | 12/2012 | Garvey et al. |
| 8,539,813 B2 | 9/2013 | Cain et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2010/0011845 A1 | 1/2010 | Laugharn et al. |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0305432 A1 | 12/2010 | Duhay et al. |
| 2010/0317971 A1 | 12/2010 | Fan et al. |
| 2011/0040190 A1 | 2/2011 | Jahnke et al. |
| 2011/0054315 A1 | 3/2011 | Roberts et al. |
| 2011/0054363 A1 | 3/2011 | Cain et al. |
| 2011/0112400 A1 | 5/2011 | Emery et al. |
| 2011/0118602 A1 | 5/2011 | Weng et al. |
| 2011/0172529 A1 | 7/2011 | Gertner |
| 2011/0178444 A1 | 7/2011 | Slayton et al. |
| 2011/0251528 A1 | 10/2011 | Canney et al. |
| 2011/0257524 A1 | 10/2011 | Gertner |
| 2011/0263967 A1 | 10/2011 | Bailey et al. |
| 2012/0010541 A1 | 1/2012 | Cain et al. |
| 2012/0029353 A1 | 2/2012 | Slayton et al. |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0130288 A1 | 5/2012 | Holland et al. |
| 2012/0172720 A1 | 7/2012 | Kawabata |
| 2012/0189998 A1 | 7/2012 | Kruecker et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0041293 A1 | 2/2013 | Cain |

(56) References Cited

U.S. PATENT DOCUMENTS

| | | |
|---|---|---|
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0190623 A1 | 7/2013 | Bertolina et al. |
| 2013/0269982 A1 | 10/2013 | Teofilovic |
| 2013/0289593 A1 | 10/2013 | Hall et al. |
| 2013/0303906 A1 | 11/2013 | Cain et al. |
| 2014/0058293 A1 | 2/2014 | Hynynen et al. |
| 2014/0073995 A1 | 3/2014 | Teofilovic et al. |
| 2014/0100459 A1 | 4/2014 | Xu et al. |
| 2014/0128734 A1 | 5/2014 | Genstler et al. |
| 2015/0375015 A1 | 12/2015 | Cain |
| 2016/0135916 A1 | 5/2016 | Rakic et al. |

FOREIGN PATENT DOCUMENTS

| | | |
|---|---|---|
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| GB | 2099582 A | 12/1982 |
| JP | 60-80779 A | 5/1985 |
| JP | 61-196718 A | 8/1986 |
| JP | HEI 2-215451 | 8/1990 |
| JP | HEI 6-197907 A | 7/1994 |
| JP | HEI 7/504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | HEI 10-512477 | 12/1998 |
| JP | 2000300559 A | 10/2000 |
| JP | 2003-510159 A | 3/2003 |
| JP | 2004-505660 A | 2/2004 |
| JP | 2005167058 A | 6/2005 |
| JP | 2007520307 A | 7/2007 |
| JP | 2010019554 A | 1/2010 |
| JP | 2010029650 A | 2/2010 |
| JP | 2010204068 A | 9/2010 |
| JP | 2004-512502 A | 4/2014 |
| WO | WO 94/06355 A1 | 3/1994 |
| WO | WO 02/32506 A1 | 4/2002 |
| WO | WO2005/018469 A1 | 3/2005 |
| WO | WO 2008/051484 A2 | 5/2008 |
| WO | WO2011/040054 A1 | 7/2011 |
| WO | WO 2011/092683 A1 | 8/2011 |
| WO | WO2011/154654 A2 | 12/2011 |
| WO | WO2015/000953 A1 | 1/2015 |

OTHER PUBLICATIONS

Avtech; AVR-8 Data sheet; May 23, 2004; 3 pages; retrieved from the internet (http//www.avtechpulse.com).
Lin et al.; U.S. Appl. No. 14/656,633 entitled "Frequency compounding ultrasound pulses for imaging and therapy," filed Mar. 12, 2015.
Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Jahnke et al.; U.S. Appl. No. 14/746,692 entitled "Disposable acoustic coupling medium container," filed Jun. 22, 2015.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.•, vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Bjoerk et al.; Cool/MOS CP—How to make most beneficial use of the generation of super junction technology devices. lnfineon Technologies AG. Feb. 2007 [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vase Intery Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.

(56) References Cited

OTHER PUBLICATIONS

Hartmann; Ultrasonic properties of poly(4-methyl pentene-1), Journal of Applied Physics, vol. 51, pp. 310-314, Jan. 1980.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43 (10); pp. 3113-3128; Oct. 1998.
Hynynen et al.; Tissue thermometry during ultrasound exposure; European Urology; 23(Suppl 1); pp. 12-16; 1993 (year of pub. sufficiently earlier than effective US filing date and any foreign priority date).
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Noninvasive Thrombolysis Using Pulsed Ultrasound Cavitation Therapy Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument).
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Van Kervel et al.; A calculation scheme for the optimum design of ultrasonic transducers; Ultrasonics, vol. 21, pp. 134-140, May 1983.

(56) References Cited

OTHER PUBLICATIONS

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009 (author manuscript).

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Arani et al.; Transurethral prostate magnetic resonance elestography; prospective imaging requirements; Magn. Reson. Med.; 65(2); pp. 340-349; Feb. 2011.

Avago Technologies; Avago's ACNV2601 optocoupler is an optically coupled logic gate; Data Sheet; 2 pages; Jul. 29, 2010.

Billson et al.; Rapid prototyping technologies for ultrasonic beam focussing in NDE; IEEE International Ultrasonic Symposium Proceedings; pp. 2472-2472; Oct. 2011.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS); 2012 IEEE International; 8 pages; Oct. 7-10, 2012.

Cain et al.; U.S. Appl. No. 14/911,273 entitled "Histotripsy using very short ultrasound pulses," filed Feb. 10, 2016.

Hobarth et al.; Color flow doppler sonography for extracorporal shock wave lithotripsy; Journal of Urology; 150(6); pp. 1768-1770; Dec. 1, 1993.

Maxwell et al.; In-vivo study of non-invasive thrombolysis by histotripsy in a porcine model; IEEE international Ultrasonics Symposium; IEEE; p. 220-223; Sep. 20, 2009.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Wikipedia; Medical ultrasound; 15 pages; retrieved from the internet (https://en.wikipedia.org/w/index.php?title=Medical_utrasound &oldid=515340960) on Jan. 12, 2018.

\* cited by examiner

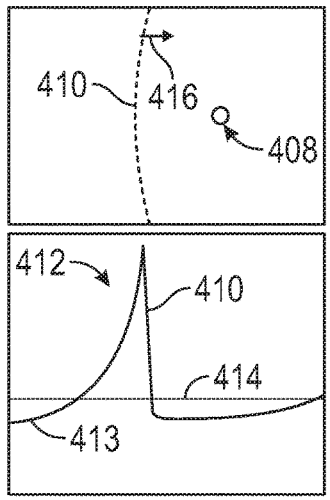 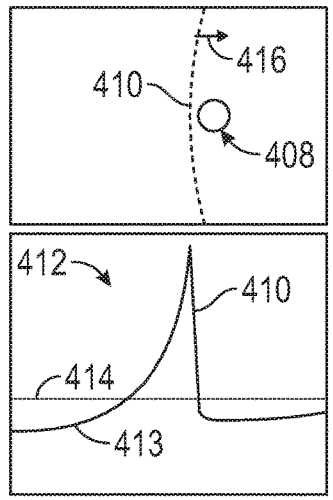 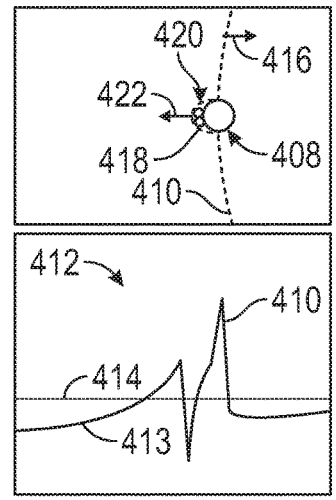
FIG. 4a  FIG. 4b  FIG. 4c
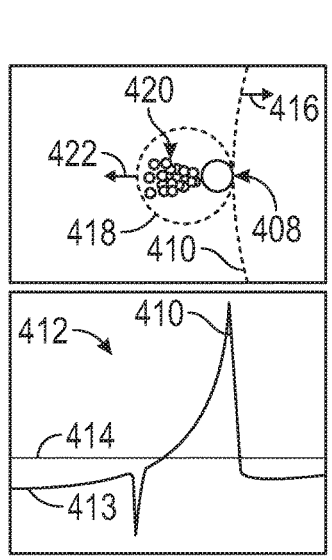 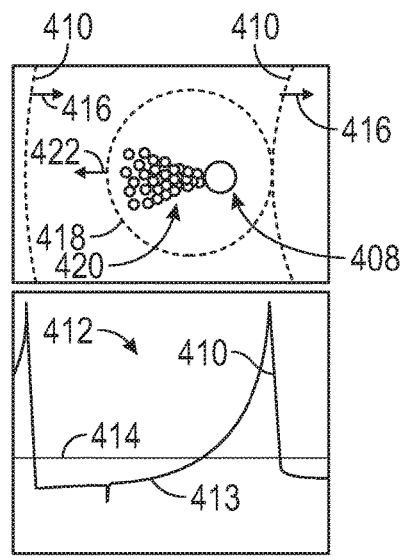
FIG. 4d  FIG. 4e

HISTOTRIPSY EXCITATION SEQUENCES OPTIMIZED FOR BUBBLE CLOUD FORMATION USING SHOCK SCATTERING

CROSS REFERENCE TO RELATED APPLICATIONS

This application claims the benefit under 35 U.S.C. 119 of U.S. Provisional Patent Application No. 61/842,820, filed Jul. 3, 2013, titled "Modulated Excitation Sequences for Enhanced Pulsed Ultrasound Cavitational Therapy", which application is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to treating tissue with cavitation created by ultrasound therapy.

BACKGROUND

Histotripsy, or pulsed ultrasound cavitation therapy, is a technology where short, intense bursts of acoustic energy induce controlled cavitation (microbubble or bubble cloud formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high pressure amplitude acoustic pulses with low duty cycle.

Compared with conventional focused ultrasound technologies, Histotripsy has important advantages: 1) the destructive process at the focus is mechanical, not thermal; 2) bubble clouds appear bright on ultrasound imaging thereby confirming correct targeting and localization of treatment; 3) treated tissue appears darker (hypoechoic) on ultrasound imaging, so that the operator knows what has been treated; and 4) Histotripsy produces lesions in a controlled and precise manner. It is important to emphasize that unlike microwave, radiofrequency, or high-intensity focused ultrasound (HIFU), Histotripsy is not a thermal modality.

Early canine studies of Histotripsy homogenization of prostate tissue employed a therapy transducer that was positioned to deliver Histotripsy transabdominally. In these studies, the prostate was located only a short distance from the skin surface and there was a relatively wide path from the transducer through the skin to focus ultrasound energy. Consequently, the spherical Histotripsy therapy transducer employed in these studies had 14 cm aperture and 10 cm focal length (F-number=0.71). Histotripsy therapy transducers with high F-numbers have very low efficiency compared to transducers with low F-numbers. These inefficiencies are primarily due to nonlinear acoustic propagation leading to shockwave formation.

Specialized therapy transducer and drive electronics have been designed to focus Histotripsy therapy through the perineum to the prostate. One example of a therapy transducer 100 configured to deliver Histotripsy therapy to the prostate is shown in FIG. 1. The transducer 100 can comprise a plurality of ultrasound transducer elements 102 disposed within housing 104. The transducer can be connected to a waveform generator configured to deliver Histotripsy waveforms from the transducer to tissue. The prostate depth from this approach is significantly deeper than in the canine model above. Additionally, the skeletal anatomy of the pelvis and transrectal position of the ultrasound imaging probe significantly reduced the effective transducer aperture. A cut-out 106 in the lower perimeter of housing can be configured to accommodate an ultrasound imaging probe (not shown) which has an F-number=0.85 in the main diameter and F-number=0.98 at the cut out.

Based on bench-top experimentation and modeling, an initial set of therapy transducer excitation parameters (3 cycles/pulse, 750 Vpp, 500 Hz PRF (Pulse Repetition Frequency)) was selected for canine testing with this transducer. This excitation sequence produced a non-linear focal pressure waveform with a peak negative and peak positive pressure of approximately 25 MPa and 100 MPa in water. We define this sequence and its variants as a, standard, or non-optimized, sequence because the sequence parameters were not optimized for bubble cloud formation.

This standard excitation sequence and variants were used to treat approximately 30 canine subjects to establish feasibility, dosing (cumulative number of pulses), and treatment implementation guidelines. An additional 10 canine subjects were then treated in a confirmatory study. Although, these studies yielded outstanding efficacy results, the observation of apparent minor injury (subclinical fibrosis) to the prefocal abdominal rectus muscle in 2 of 10 subjects in the confirmatory trial led to the conclusion that the safety profile needed to be improved by developing Histotripsy pulse sequences that deliver energy more efficiently. It is likely that the need to improve the efficiency of Histotripsy will become more important as transducers are developed to go deeper into tissues through skeletal anatomical obstructions.

SUMMARY OF THE DISCLOSURE

Improved efficiency leading to pre-focal heat reduction is imperative when soft tissue is targeted deep beneath the skin surface through skeletal anatomical obstructions which require ultrasound therapy transducers that have relatively high F numbers (F-number >0.8). Sequences optimized for enhanced Histotripsy homogenization of soft tissues were developed to reduce the potential of pre-focal thermal injury by optimizing the sequence efficiency. Improved efficiency of optimized excitation sequences increases the probability of initiating Histotripsy bubble clouds in tissue and reduces the occurrences of extinguishing bubble clouds when translating through tissues. Additionally, optimized sequences can be designed to selectively ablate fibrous tissues or ablate less dense tissues while preserving more fibro-elastic vital structures such as neuro-vascular structures.

Effective optimized sequences for high F-number transducers are characterized by an initiation pulse which is designed to create a least a single acoustically generated nucleus (bubble), followed by a shock scattering pulse (hereafter referred to as a scattering pulse or scattering pressure waveform) after an optimized time delay to enable a shockwave to impinge upon the first bubble to create a bubble cloud. Subsequent scattering pulses can follow also with optimized timing in order to further maintain the effectiveness of the bubble cloud. Note that pulse and pressure waveform will be used interchangeably in this application.

A method of treating tissue with ultrasound energy, comprising the steps of delivering an initiation pressure waveform from an ultrasound therapy transducer into tissue, the initiation pressure waveform being configured to produce at least one bubble in the tissue, delivering a scattering pressure waveform from the ultrasound therapy transducer into the at least one bubble within a life-cycle of the at least one bubble, and producing cavitation nuclei near the at least one bubble with the scattering pressure waveform.

In some embodiments, the scattering pressure waveform is delivered within 5 µs to 200 µs of the initiation pressure waveform.

In one embodiment, the method further comprises repeating the delivering an initiation pressure waveform and delivering a scattering pressure waveform steps until treatment of the tissue is completed.

In one embodiment, a pressure amplitude and/or number of cycles of the initiation pressure waveform is minimized to reduce tissue heating.

In another embodiment, a peak-to-peak pressure of the scattering pressure waveform is sufficient in amplitude create additional cavitation nuclei in the focal region.

In alternative embodiments, the pressure amplitude and/or number of cycles of the scattering pressure waveform is minimized to reduce tissue heating.

In some embodiments the method further comprises, after delivering the scattering pressure waveform, delivering a second scattering pressure waveform towards the at least one bubble and the cavitation nuclei.

In some embodiments, the second scattering pressure waveform is delivered within 5 µs to 1 s of the scattering pressure waveform.

In another embodiment, the method further comprises delivering additional scattering pressure waveforms without delivering additional initiation pressure waveforms until the at least one bubble and/or the cavitation nuclei no longer remain in the tissue.

In some embodiments, the additional scattering pressure waveforms are delivered every 5 µs to 1 s.

In one embodiment, a pulse sequence comprising the initiation pressure waveform and the scattering pressure waveform has a sequence PRF ranging from 1-5000 Hz.

In other embodiments, the scattering pressure waveform delivers less energy to intervening tissue than the initiation pressure waveform.

In one embodiment, the initiation pressure waveform and the scattering pressure waveform have substantially similar pressure amplitudes. In another embodiment, a pressure amplitude of the scattering pressure waveform is less than a pressure amplitude of the initiation pressure waveform. In alternative embodiments, a pressure amplitude of the scattering pressure waveform is more than a pressure amplitude of the initiation pressure waveform.

A method of treating tissue with ultrasound energy is provided, comprising the steps of transmitting an initiation pressure waveform from an ultrasound therapy transducer into tissue, the initiation pressure waveform being configured to produce at least one bubble in the tissue, during a life-cycle of the at least one bubble, transmitting a scattering pressure waveform from the ultrasound therapy transducer into the at least one bubble, the scattering pressure waveform configured to become a shocked focal pressure waveform in the tissue having a shocked positive pressure half cycle and a shocked negative pressure half cycle, the shocked positive pressure half cycle being configured to impinge on the at least one bubble and to scatter, invert, and constructively interfere with the shocked negative pressure half cycle to form a negative pressure half cycle waveform, and producing cavitation nuclei near the at least one bubble with a shock scattering mechanism between the positive pressure half cycle waveform and the at least one bubble.

A method of delivering ultrasound energy to tissue is provided, comprising the steps of delivering an initiation pulse from an ultrasound therapy transducer configured to provide at least 5 MPa of peak negative pressure to produce at least one bubble in the tissue, delivering a first scattering pulse into the at least one bubble within 5 µs to 200 µs of the initiation pulse, and producing a cavitation cloud of nuclei near the at least one bubble with a shock scattering mechanism between the first scattering pulse and the at least one bubble.

An ultrasound therapy system is provided, comprising an ultrasound therapy transducer, and an ultrasound therapy generator coupled to the ultrasound therapy transducer, the ultrasound therapy generator configured to drive the ultrasound therapy transducer to deliver an initiation pressure waveform into tissue to produce at least one bubble in tissue, the ultrasound therapy generator being further configured to drive the ultrasound therapy transducer to deliver a first scattering pressure waveform within 5 µs to 200 µs of the initiation pressure waveform into the at least one bubble to produce cavitation nuclei near the at least one bubble.

In some embodiments, a peak to peak pressure of the first scattering pulse is sufficient in pressure amplitude to produce cavitation nuclei near the at least one bubble.

In other embodiments, the ultrasound therapy generator is further configured to drive the ultrasound therapy transducer to deliver at least one additional scattering pulse after the first scattering pressure waveform to produce cavitation nuclei near the at least one bubble.

In one embodiment, the ultrasound therapy generator further comprises a controller configured to generate complex waveforms to initiate the initiation and scattering pressure waveforms, a high voltage power supply coupled to the controller, an amplifier configured to receive and amplify the complex waveforms from the controller and high voltage power supply, and a matching network configured to match an impedance of the ultrasound therapy transducer to the amplifier.

A method of treating tissue with ultrasound energy is provided, comprising the steps of producing at least one bubble in the tissue with ultrasound energy, colliding a shocked focal pressure waveform with the at least one bubble, and forming cavitation nuclei near the at least one bubble.

In one embodiment, the colliding step is performed during a life-cycle of the at least one bubble.

In another embodiment, the colliding step is performed within 5 µs to 200 µS of the producing step.

In an alternative embodiment, the forming cavitation nuclei step is achieved with a shock scattering mechanism between the shocked focal pressure waveform and the at least one bubble.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4a-4e are conceptual drawings that illustrate shock scattering.

DETAILED DESCRIPTION

Generation of Cavitation

Several principles of cavitation nuclei and bubble cloud formation that provide important background information for the development of the preferred embodiment are disclosed herein. Cavitation nuclei are individual bubbles formed as a result of the delivery of low pressure to tissue. Bubble clouds can comprise of dense clusters of cavitation nuclei that form at or near the transducer focus. The formation of cavitation nuclei (bubble clouds) are both key components of Histotripsy therapy.

Probability for Forming Cavitation Nuclei

Cavitation nuclei can be formed in tissue if the tissue is subjected to a peak negative (peak rarefaction) pressure approaching or exceeding the pressure level needed to create at least a single cavitation nucleus (bubble). Note that this level is variable and is dependent upon multiple factors including tissue properties (structure and composition, dissolved gas content, and existence of impurities), transducer geometry (focal distance and f number), and sequencing scheme (PRF; number of cycles). The number of cavitation nuclei formed from one acoustic pulse has been shown to be directly related to the peak negative pressure achieved.

Cavitation Time Course

Figure 1:
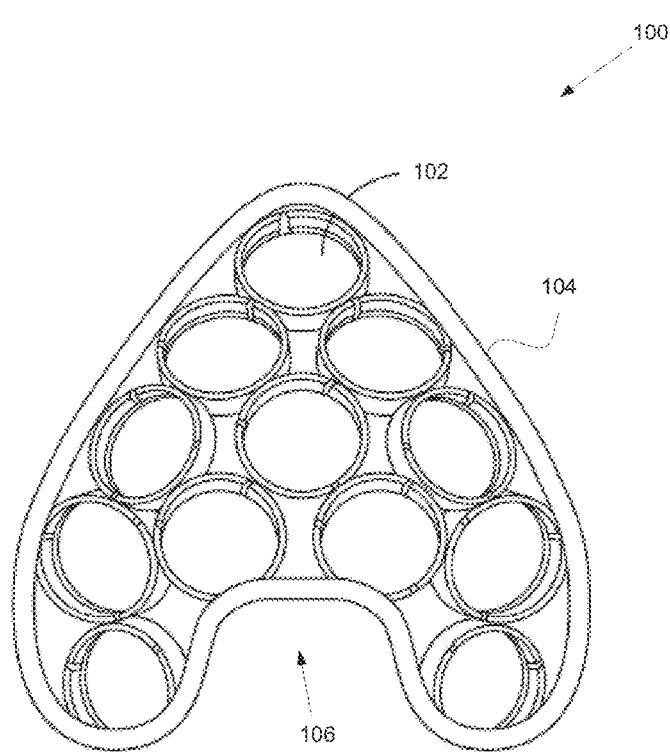
FIG. 1 is an ultrasound therapy transducer according to one embodiment.
Figures 2A, 2B, 2C:
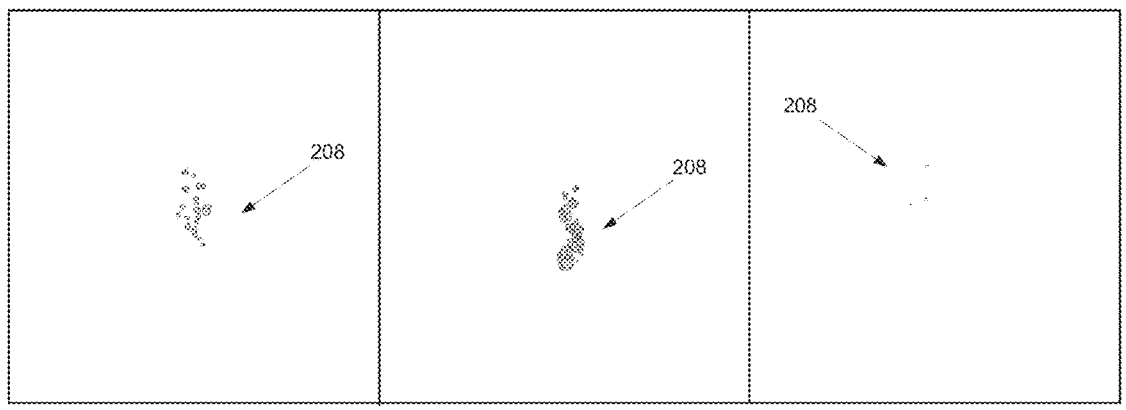
FIGS. 2a-2c are illustrations of bubble cloud initiation in water.

Cavitation nuclei grow to a maximum size and then collapse. The cavitation time course for the process of bubble initiation, growth, and then collapse is dependent on the medium (i.e., tissue type). The cavitation time course for liquids is longer than in gelatin and soft tissue. Table 1 compares cavitation initiation, growth, and collapse times in water vs. gelatin. FIGS. 2a-2c are illustrations showing a typical cavitation time course. FIG. 2a illustrates initiation of cavitation 208 in a medium, such as in tissue, in water, or in gelatin. FIG. 2b shows growth of the cavitation 208 to a maximum size, in which the cavitation bubbles are grouped together in the focal zone. FIG. 2c illustrates collapse of the cavitation 208 where nearly all the cavitation bubbles have collapsed and disappeared.

|  | Delay-time | |
| --- | --- | --- |
| Event | In Water (µs) | In Gelatin (µs) |
| Initiation | 68 | 68 |
| Growth | 149 | 84 |
| Collapse | 230 | 100 |

Acoustic Shock and the Shock Scattering Mechanism for Bubble Cloud Formation

Figure 3:
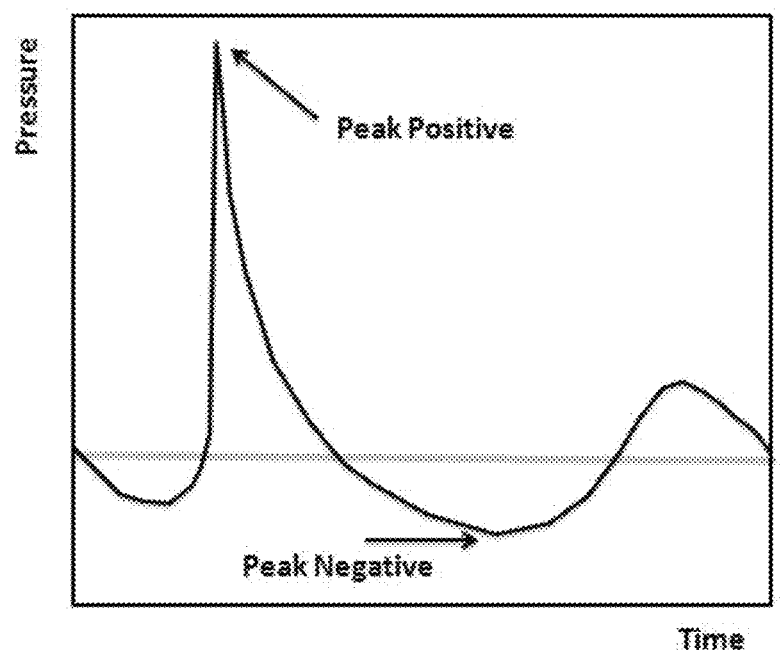
FIG. 3. illustrates a focal pressure waveform according to one embodiment.

As a sound waveform travels through the medium the positive (compression) half cycle(s) travel faster than the negative (rarefaction) half cycle(s). This effect causes the pressure waveform to become nonlinear creating a sharp transition between negative and positive half cycles of the pressure waveform. The pressure amplitude of the positive half cycle increases as the slope of this transition increases and the pressure waveform is said to be become more nonlinear or "shocked". This can be referred to as a shocked focal pressure waveform. The level of nonlinearity is dependent upon the pressure amplitude of the pressure waveform as well as the distance propagated through the medium. FIG. 3 shows an example of a shocked focal pressure waveform with a positive half cycle and a negative half cycle. It should be understood that shocked focal pressure waveforms can include a plurality of positive and negative half cycles.

According to the present disclosure, cavitation nuclei can be formed in tissue as a result of shock scattering. Shock scattering occurs when a shocked positive pressure half cycle of an acoustic waveform is reflected, or scattered, off of a pre-existing bubble(s) and the shocked positive pressure half cycle is consequently inverted such that it combines with the incident negative pressure half cycle of the acoustic waveform in an additive fashion. If this combined new negative pressure half cycle produced is large enough (i.e. above the intrinsic threshold for the tissue or medium of interest—greater than 5 MPa peak negative pressure for example), additional cavitation nuclei will form near any preexisting nuclei. This process repeats itself until the combined new negative pressure half cycle is not sufficient in pressure to create new cavitation nuclei.

FIGS. 4a-4e are conceptual drawings illustrating a shock scattering method of Histotripsy therapy. The frames on the top show a pre-existing bubble 408 and a shocked positive pressure half cycle 410, and the frames on the bottom show the ultrasound pulse pressure distribution 412 (horizontal line 414 indicates a pressure amplitude of zero). The pre-existing bubble 408 may be formed with an initiation pulse or sequence as described above. A shocked pressure waveform can then be transmitted towards the bubble 408 during a life-cycle of the bubble according to one embodiment of the shock scattering method.

In FIGS. 4a-4e, the incident shocked pressure waveform 412 propagates from left to right towards the pre-existing bubble 408, as indicated by arrows 416. The incident shocked pressure waveform can be delivered towards and into the bubble during a life-cycle of the bubble, so that the incident shocked pressure waveform interacts with the bubble. A single pre-existing bubble 408 is shown in FIG. 4a, having already been generated in the tissue as described above. That bubble can expand in size, as shown in FIG. 4b, due to the initial negative pressure half cycle of the incident shocked pressure waveform. In FIG. 4c, a shocked positive pressure half cycle 410 of the incident shocked pressure waveform 412 impinges on the bubble 408 and the positive pressure half cycle begins to scatter. The scattered shocked positive pressure half cycle inverts and constructively interferes with the shocked negative pressure half cycle 413 of the incident shocked pressure waveform 412 to create a transient, large amplitude, negative pressure half cycle 418 (illustrated as the circular dotted line 418 in FIGS. 4c-4e) that produces additional cavitation nuclei 420 near or behind the bubble 408. The negative pressure half cycle 418 propagates from right to left, as indicated by arrows 422. The additional cavitation nuclei 420 form in the opposite direction of the shocked positive pressure waveform 410, until the negative pressure half cycle 418 drops below the threshold for the formation of cavitation nuclei, as shown in FIG. 4e. This process may be repeated with successive shocked pressure waveforms transmitted towards and into the pre-existing bubble 408 and additional cavitation nuclei 420.

Cavitation nuclei formed by this shock scattering method tend to grow towards the therapy transducer and their extent depends on the number of high pressure cycles in the pulse (waveform) and the pulse repetition frequency (PRF). Minimizing the number of cycles in a shocked waveform or reducing the sequence PRF are effective ways of reducing the length of the bubble cloud and also reducing the time average intensity and therefore the thermal dose.

Enhanced Bubble Cloud Formation Using Shock Scattering

The key components of a preferred Histotripsy excitation sequence described in this disclosure are: 1) A first pulse of the sequence, referred to as an initiation pulse or initiation pressure waveform, configured to form at least one bubble in the tissue 2) A second pulse of the sequence, referred to as a scattering pulse or scattering pressure waveform, configured to generate cavitation nuclei near the at least one bubble through shock scattering, and 3) A specific time delay between the initiation and scattering pulses.

The key parameters for the pulses are: The initiation pulse should be configured to produce at least one bubble in the tissue of interest. This can be achieved with a traditional Histotripsy initiation pulse, as described above, or with other ultrasound techniques that can induce bubble formation in tissue due to boiling such as HIFU or boiling Histotripsy. The scattering pulse should have a peak-to-peak pressure high enough for shock scattering formation of cavitation nuclei. In some embodiments, the time delay between these pulses can range between 5 μs and 200 μs. In another embodiment, the time delay between these pulses can range between 5 μs and 40 ms. In another embodiment, the time delay between these pulses can range between 5 μs and 1 s.

In another embodiment, the pressure amplitude and/or number of cycles used in the initiation pulse can be increased or decreased. Increasing the pressure amplitude and/or number of cycles in the initiation pulse may increase the probability of creating cavitation in the tissue. However this would also likely increase the time averaged intensity, and thermal dose, delivered to the tissue and the extent of the bubble cloud. Decreasing the pressure amplitude and/or number of cycles of the initiation pulse will reduce the intensity, and thermal dose, of the sequence but may limit the ability of the sequence to generate and/or maintain cavitation.

In another embodiment, the pressure amplitude and/or number of cycles used in the scattering pulse(s) can be increased or decreased. Increasing the pressure amplitude and/or number of cycles in the scattering pulse(s) may increase the probability of creating cavitation in the tissue. However this would also likely increase the time averaged intensity delivered to the tissue, and thermal dose, delivered to the tissue and the extent of the bubble cloud. Decreasing the pressure amplitude and/or number of cycles of the scattering pulse(s) will reduce the intensity, and thermal dose, of the sequence but may limit the ability of the sequence to generate and/or maintain cavitation.

The sequence PRF can be as high as 5000 Hz assuming that the time averaged intensity, and resultant thermal dose, are kept within safe limits. The preferred range depends on the tissues being treated. A higher PRF is recommended for more dense and fibrous tissues, and a low PRF is recommended for less dense tissues and for preservation of more fibrous and often vital tissues. Selective treatment of tissues with Histotripsy based on their stiffness can be a probable design and performance consideration for sequence development.

In some embodiments additional scattering pulses with lower pressure amplitude and/or number of cycles (compared with the initiation pulse pressure amplitude and/or number of cycles), can be applied in order to reduce the intensity, and thermal dose, of the sequence without reducing the sequence PRF.

Figure 5A:
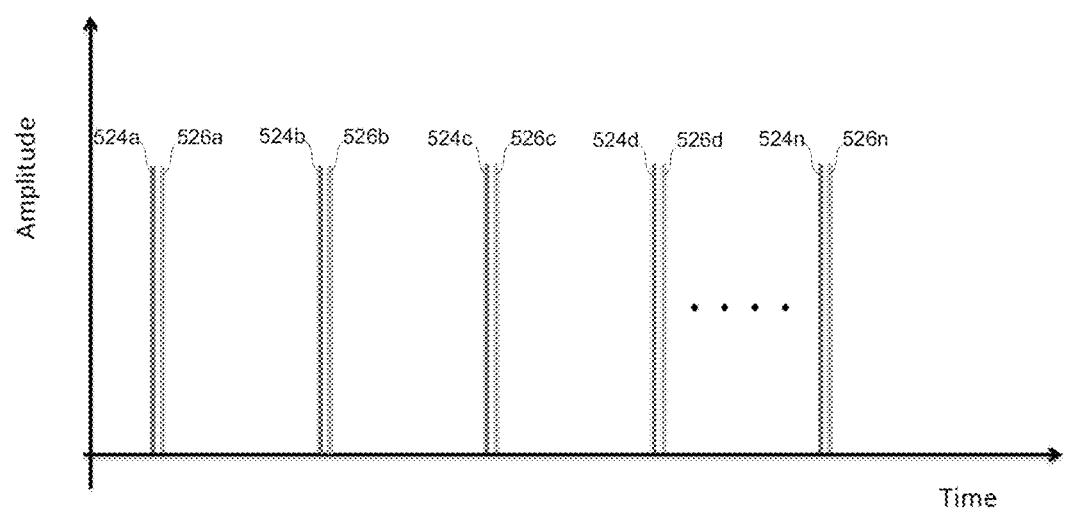
FIGS. 5a-5c illustrate various embodiments of pulse sequences that include initiation and scattering pressure waveforms for delivering ultrasound energy to tissue.
Figure 5B:
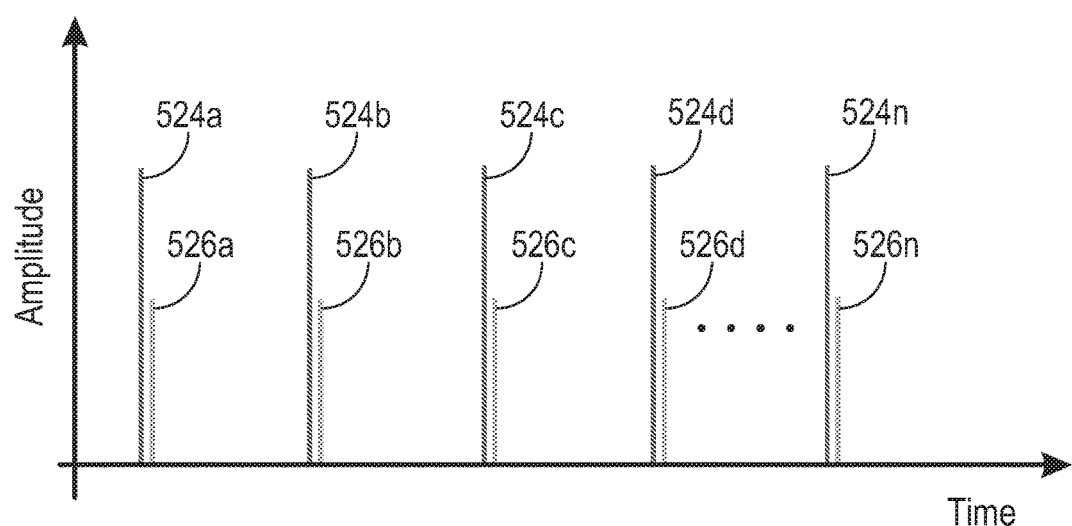
Figure 5C:
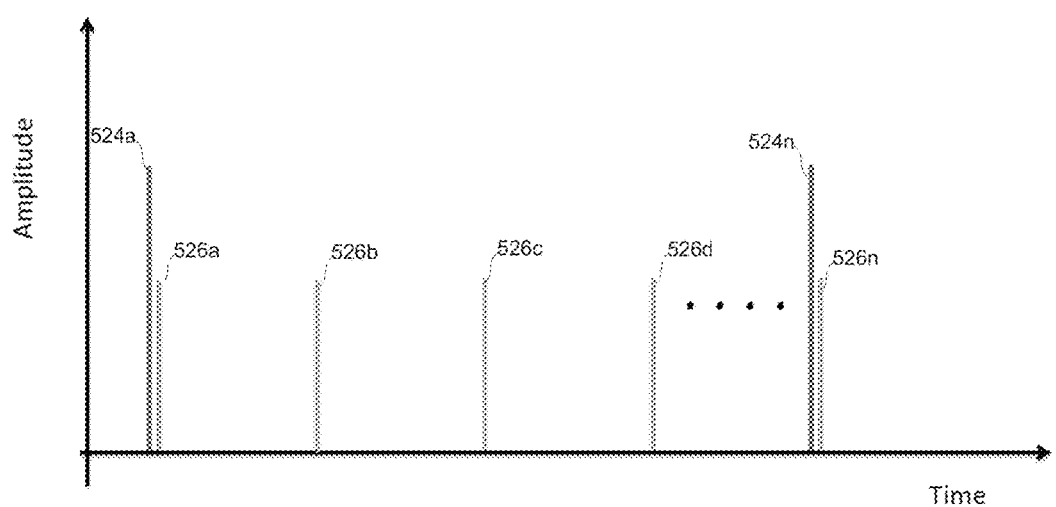

FIGS. 5a-5c illustrate three different embodiments for Histotripsy initiation and scattering pulse sequences that can be used to generate and maintain cavitation in tissue during a shocked scattering method of Histotripsy therapy. In FIG. 5a, an initiation pulse 524a comprising a pressure waveform configured to form at least one bubble in the tissue can be transmitted into tissue. After a specific time delay has passed, a scattering pulse 526a can be transmitted into tissue towards and into the at least one bubble formed by the initiation pulse 524a. In some embodiments, the specific time delay between these pulses can range between 5 μs and 200 μs. In another embodiment, the time delay between these pulses can range between 5 μs s and 40 ms. In another embodiment, the time delay between these pulses can range between 5 μs and 1 s. The scattering pulse 526a becomes a shocked focal pressure waveform as it travels through the tissue, and the at least one shocked positive pressure half cycle of the scattering pulse impinges on the at least one bubble and is scattered by the at least one bubble. The shocked positive pressure half cycle of the scattering pulse inverts and constructively interferes with the shocked negative pressure half cycle of the scattering pulse to create a transient, large amplitude, negative pressure half cycle that produces additional cavitation nuclei behind the at least one bubble generated by the initiation pulse. These pulse sequence pairs of initiation and scattering pulses can be repeated to achieve the desired ablation effect in tissue from the resulting cavitation, as shown in FIG. 5a (pulse pairs 524b/526b, 524c/526c, 524d/526d, . . . , 524n/526n). In this embodiment, the pressure amplitudes and/or number of cycles of both the initiation and scattering pulses can be the same or approximately the same.

FIG. 5b shows another embodiment, similar to the embodiment of FIG. 5a, except the pressure amplitude of the scattering pulses 524a-524n are smaller than the pressure amplitude of the corresponding initiation pulses. Due to the principle of shock, the peak positive wave is amplified relative to the peak negative wave and therefore, the pressure amplitude used to create the scattering pulses can be lowered while still delivering the needed negative pressure with the reflected and inverted positive wave. This embodiment is more efficient than the embodiment of FIG. 5a and delivers a lower dose of energy into the tissue. In another embodiment, however, the pressure amplitude of the scattering pulses can be greater than the pressure amplitude of the corresponding initiation pulses.

FIG. 5c illustrates another embodiment, which is a variation of the embodiment of FIGS. 5a and 5b. In this embodiment, initiation pulse 524a is followed by a scattering pulse 526a after a specific time delay, but instead of following that with another initiation/scattering pulse pair as in FIG. 5a, instead the scattering pulse 526a is followed with another scattering pulse 526b after a second time delay. A plurality of scattering pulses can be delivered into tissue after the appropriate time delay to maintain the effectiveness of the bubble cloud (e.g., pulses 526c, 526d) to achieve the desired ablation effect in tissue from the resulting cavitation. The pressure amplitudes of the scattering pulse can be less than, equal to, or greater than the pressure amplitude of the initiation pulse. In some embodiments, the time delay for subsequent scattering pressure waveforms can be different than the time delay used for the first scattering pressure. For example, the first scattering pressure waveform may be delivered within 5 µs to 200 µs of the initiation pressure waveform, but subsequent scattering pressure waveforms may be delivered within 5 µs to 200 µs, 5 µs to 40 ms, or 5 µs to 1 s. If the cavitation needs to be re-initiated in the tissue, the sequence can be re-started with another initiation/scattering pulse pair, as shown by 524n/526n in FIG. 5c. This embodiment also uses a lower pressure amplitude scattering pulse, as in the embodiment of FIG. 5b, but also uses fewer initiation pulses. The result of this embodiment is the lowest dose of energy delivered to tissue between the embodiments of FIGS. 5a-5c. This strategy has the potential to lower the dose significantly (as much as 50% for example) compared with traditional histotripsy sequences.

Amplitude Reduction or Elimination of the Initiation Pulse Once the Bubble Cloud is Established:

The purpose of the initiation/scattering pair is to generate cavitation in tissue with shock scattering. Once the bubble cloud is generated, and if the focus is not moved, the initiation pulse may no longer be needed to maintain the effectiveness of the bubble cloud. In this case, the system could be designed to first create a bubble cloud with an initiation/scattering pair and follow that with lower pressure amplitude (relative to the initiation pulse pressure amplitude) scattering pulses until the focus is moved. At which point the process is repeated.

System Software and Hardware Design that Allowed for Sequence Development

Figure 6:
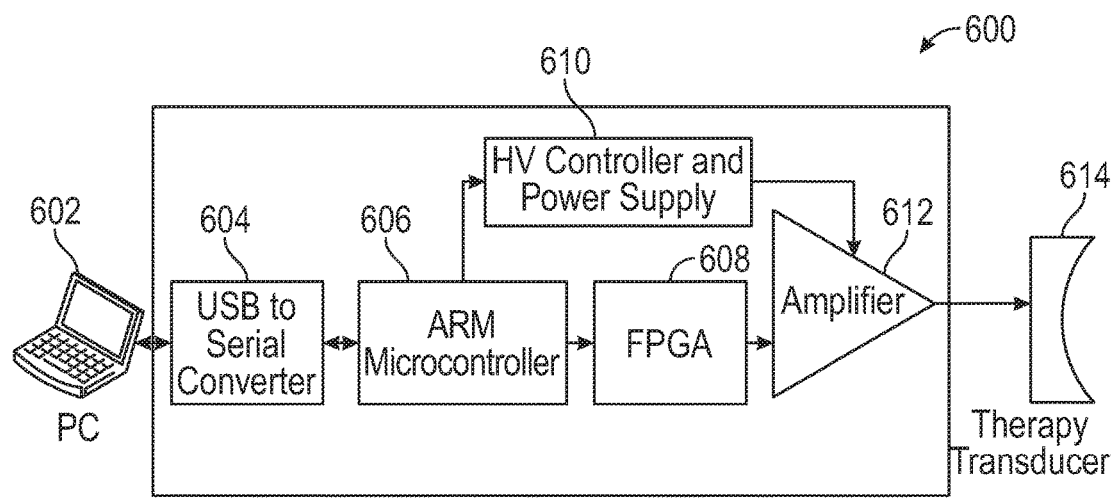
FIG. 6 illustrates a system configured to deliver the preferred sequences for treating the tissue with cavitation.

A Histotripsy system and generator is configured to generate very complex waveforms in order to support the ultrasound pulse sequences described herein. A simplified block diagram of system 600 is shown in FIG. 6. The main components of the system are: Computer/controller 602, USB to Serial Converter 604, Microcontroller 606, FPGA (Field Programmable Gate Array) 608, High Voltage Controller and Power Supply 610, Amplifier 612, and Therapy Transducer 614.

All controls for the generator can be established using "Histotripsy Service Tool" software that can run on the computer/controller 602 (e.g., a standard PC) and communicates to the generator via USB serial communication 604.

The system 600 is configured to receive multiple sets of different driving parameters and loop them, which give the ability to the user to create wide range of custom sequences where all parameters (PRF, voltage amplitude, number of cycles, number of pulses per set, frequency, transducer element channels enabled, and time delays) can be set differently for every pulse generated. Time delays between pulses can be specified by the PRF for a parameter set or by specifying zero as the number of cycles per pulse.

For overall voltage amplitude regulation, level of high voltage is changed accordingly through the Microcontroller 606 and HV Controller 610. This method cannot be used for dynamic voltage amplitude changes between two pulses since it will take too long for all capacitors on the HV line to discharge. For dynamic voltage amplitude changes between pulses, PWM (pulse width modulation) is used at the FPGA 608 where the duty cycle of the pulse is modulated in order to produce the desired pulse voltage and resultant pressure amplitude.

Histotripsy Service Tool

Histotripsy Service Tool is an application that can be run on any PC and is used for controlling the system. The Histotripsy Service Tool can start/stop the therapy, set and read the level of high voltage, therapy parameters (PRF, number of cycles, duty ratio, channel enabled and delay, etc), and set and read other service and maintenance related items.

USB to Serial Converter

USB to Serial converter 604 converts USB combination to serial in order to communicate to the Microcontroller 606.

Microcontroller

The Microcontroller 606 communicates to the computer/controller 602 (Histotripsy Service Tool) to set/read working parameters, start/stop the therapy, etc. It can use internal flash memory to store all the parameters. The Microcontroller communicates to the FPGA 608 all driving parameters that are necessary to generate complex pulsing. It also communicates using serial communication to the high voltage controller and power supply 610 where it can set/read the proper level of driving voltage.

FPGA

The FPGA 608 receives the information from the Microcontroller 606 and it generates the complex pulsing sequence that is required to drive the amplifier 612. The FPGA can run on 100 MHz clock since speed of pulsing is critical to be timed in 10 ns increments.

High Voltage Controller and Power Supply

The High Voltage Controller and Power Supply 610 receives the commands from the Microcontroller 606 regarding the level of DC voltage that needs to be supplied to the amplifier circuitry in order to have an adequate voltage amplitude level at the output of the amplifier.

Amplifier

The Amplifier 612 receives pulses generated by the FPGA and is supplied with high voltage from High Voltage Controller and Power Supply. It generates high voltage amplitude pulses that are fed to the Therapy Transducer 614 through the matching network components which properly matches the impedance of the therapy transducer to the impedance of the amplifier. It is necessary to use a large number of capacitors that can store enough energy to support peak current demand during the generation of high voltage amplitude pulses.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating tissue with ultrasound energy, comprising the steps of:
   delivering a first pulse of a Histotripsy excitation sequence from an ultrasound therapy transducer, the first pulse comprising an initiation pressure waveform configured to produce at least one bubble in the tissue;
   delivering a second pulse of the Histotripsy excitation sequence from the ultrasound therapy transducer, the second pulse comprising a scattering pressure waveform configured to interact with the at least one bubble within a life-cycle of the at least one bubble; and
   producing cavitation nuclei near the at least one bubble with the scattering pressure waveform.

2. The method of claim 1, wherein the scattering pressure waveform is delivered within 5 μs to 200 μs of the initiation pressure waveform.

3. The method of claim 1, further comprising repeating the delivering the initiation pressure waveform and delivering the scattering pressure waveform steps until treatment of the tissue is completed.

4. The method of claim 1, wherein a peak-to-peak pressure of the scattering pressure waveform is sufficient in amplitude create additional cavitation nuclei in the focal region.

5. The method of claim 1, further comprising, after delivering the scattering pressure waveform, delivering a second scattering pressure waveform towards the at least one bubble and the cavitation nuclei.

6. The method of claim 5, wherein the second scattering pressure waveform is delivered within 5 μs to 1 s of the scattering pressure waveform.

7. The method of claim 5, further comprising delivering additional scattering pressure waveforms without delivering additional initiation pressure waveforms until the at least one bubble and/or the cavitation nuclei no longer remain in the tissue.

8. The method of claim 7, wherein the additional scattering pressure waveforms are delivered every 5 μs to 1 s.

9. The method of claim 1, wherein the Histotripsy excitation sequence comprising the initiation pressure waveform and the scattering pressure waveform has a sequence pulse repetition frequency ranging from 1-5000 Hz.

10. The method of claim 1, wherein the scattering pressure waveform delivers less energy to intervening tissue than the initiation pressure waveform.

11. The method of claim 1, wherein the initiation pressure waveform and the scattering pressure waveform have similar pressure amplitudes.

12. The method of claim 1, wherein a pressure amplitude of the scattering pressure waveform is less than a pressure amplitude of the initiation pressure waveform.

13. The method of claim 1, wherein a pressure amplitude of the scattering pressure waveform is more than a pressure amplitude of the initiation pressure waveform.

14. A method of treating tissue with ultrasound energy, comprising the steps of:
    transmitting a first pulse of a Histotripsy excitation sequence from an ultrasound therapy transducer, the first pulse comprising an initiation pressure waveform configured to produce at least one bubble in the tissue;
    during a life-cycle of the at least one bubble, transmitting a second pulse of the Histotripsy excitation sequence from the ultrasound therapy transducer, the second pulse comprising a scattering pressure waveform configured to interact with the at least one bubble, the scattering pressure waveform configured to become a shocked focal pressure waveform in the tissue having a shocked positive pressure half cycle and a shocked negative pressure half cycle, the shocked positive pressure half cycle being configured to impinge on the at least one bubble and to scatter, invert, and constructively interfere with the shocked negative pressure half cycle to form a negative pressure half cycle waveform; and
    producing cavitation nuclei near the at least one bubble with a shock scattering mechanism between the positive pressure half cycle waveform and the at least one bubble.

15. A method of delivering ultrasound energy to tissue, comprising the steps of:
    delivering a first pulse of a Histotripsy excitation sequence from an ultrasound therapy transducer, the first pulse comprising an initiation pulse configured to provide at least 5 MPa of peak negative pressure to produce at least one bubble in the tissue;
    delivering a second pulse of the Histotripsy excitation sequence from the ultrasound therapy transducer, the second pulse comprising a first scattering pulse configured to interact with the at least one bubble within 5 μs to 200 μs of the initiation pulse; and
    producing a cavitation cloud of nuclei near the at least one bubble with a shock scattering mechanism between the first scattering pulse and the at least one bubble.

16. An ultrasound therapy system, comprising:
    an ultrasound therapy transducer; and
    an ultrasound therapy generator coupled to the ultrasound therapy transducer, the ultrasound therapy generator configured to drive the ultrasound therapy transducer to deliver a first pulse of a Histotripsy excitation sequence comprising an initiation pressure waveform into tissue to produce at least one bubble in tissue, the ultrasound therapy generator being further configured to drive the ultrasound therapy transducer to deliver a second pulse of the Histotripsy excitation sequence comprising a first scattering pressure waveform within 5 μs to 200 μs of the initiation pressure waveform into the at least one bubble to produce cavitation nuclei near the at least one bubble.

17. The system of claim 16, wherein a peak to peak pressure of the first scattering pulse is sufficient in pressure amplitude to produce cavitation nuclei near the at least one bubble.

18. The system of claim 16, wherein the ultrasound therapy generator is further configured to drive the ultrasound therapy transducer to deliver at least one additional scattering pulse after the first scattering pressure waveform to produce cavitation nuclei near the at least one bubble.

19. The system of claim 16, wherein the ultrasound therapy generator further comprises:
- a controller configured to generate complex waveforms to initiate the initiation and scattering pressure waveforms;
- a high voltage power supply coupled to the controller;
- an amplifier configured to receive and amplify the complex waveforms from the controller and high voltage power supply; and
- a matching network configured to match an impedance of the ultrasound therapy transducer to the amplifier.

* * * * *